US011957970B2

United States Patent
Knutzen et al.

(10) Patent No.: US 11,957,970 B2
(45) Date of Patent: Apr. 16, 2024

(54) DENTAL GUARD AND TRAY AND METHOD OF FORMING SUCH

(71) Applicant: Dentek Oral Care, Inc., Maryville, TN (US)

(72) Inventors: Josef V Knutzen, Allendale, NJ (US); Joseph R Martone, Bristol, CT (US); Frank M Lesniak, Media, PA (US)

(73) Assignee: DENTEK ORAL CARE, INC., Tarrytown, NY (US)

( * ) Notice: Subject to any disclaimer, the term of this patent is extended or adjusted under 35 U.S.C. 154(b) by 502 days.

(21) Appl. No.: 16/106,786

(22) Filed: Aug. 21, 2018

(65) Prior Publication Data

US 2020/0061440 A1 Feb. 27, 2020

(51) Int. Cl.
*A63B 71/08* (2006.01)

(52) U.S. Cl.
CPC ........ *A63B 71/085* (2013.01); *A63B 2209/00* (2013.01)

(58) Field of Classification Search
CPC .............. A63B 71/085; A63B 2209/00; A63B 2071/086; A63B 2071/088; A63B 71/08; A61C 7/08; A61C 9/0006; A61C 9/00; A61C 5/90; A61C 19/04; A61C 19/05; A61C 19/045; A61F 5/56; A61F 2005/563; A61F 5/566; A61F 5/58
USPC .......... 128/862, 861, 859; 433/6, 34, 37, 48, 433/38, 44
See application file for complete search history.

(56) References Cited

U.S. PATENT DOCUMENTS

| 4,776,792 A | 10/1988 | Wagner et al. |
| 5,511,562 A * | 4/1996 | Hancock .................. A61F 5/00 128/859 |
| 5,836,761 A * | 11/1998 | Belvedere ............ A63B 71/085 433/6 |
| 8,453,650 B1 * | 6/2013 | Frey ........................ A61C 5/90 128/859 |

(Continued)

FOREIGN PATENT DOCUMENTS

WO 20180089862 5/2018

OTHER PUBLICATIONS

Knutzen, Josef V.; Extended European Search Report for Application No. 18197261.3, filed Sep. 27, 2018, dated Apr. 29, 2019, 9 pages.

(Continued)

*Primary Examiner* — Victoria Hicks Fisher
(74) *Attorney, Agent, or Firm* — Taylor English Duma LLP

(57) ABSTRACT

A dental guard and tray, includes a thermoplastic dental guard, and a generally rigid tray fittingly receiving the dental guard during heating and fitting of the dental guard to teeth of the user. The dental guard includes a pair of bite pads positionable below rear teeth of the user and a connection band that connects between the bite pads and is positionable behind upper or lower front teeth of the user. The rigid tray includes a pair of bite pad supports and a connecting arc, the bite pad supports each providing a planar depression or well for receiving one of the bite pads, the connecting arc spanning between the bite pads and having fingers located proximate a midpoint of the arc and configured to angle rearwardly and upwardly from the connecting arc so as to underlie and receive the band when the dental guard is received onto the tray.

16 Claims, 9 Drawing Sheets

(56) References Cited

U.S. PATENT DOCUMENTS

| | | | |
|---|---|---|---|
| 2003/0138754 A1* | 7/2003 | DiMarino | A61C 9/0006 |
| | | | 433/37 |
| 2006/0201520 A1* | 9/2006 | Christensen, III | A61C 9/0006 |
| | | | 128/848 |
| 2013/0247923 A1* | 9/2013 | Cook | A63B 71/085 |
| | | | 128/862 |
| 2015/0004555 A1* | 1/2015 | Frey | A61F 5/566 |
| | | | 433/6 |

OTHER PUBLICATIONS

Knutzen, Josef V.; Office Action for European Application No. 18197261.3, filed Sep. 27, 2018, dated Feb. 22, 2021, 7 pages.

* cited by examiner

DENTAL GUARD AND TRAY AND METHOD OF FORMING SUCH

FIELD

This disclosure relates to the field of dental guard devices. More particularly, the disclosure relates to a system for improving fit of dental guards of the type initially softened by immersion in heated water and then placed in the mouth for fitting of the dental guard and the method of forming such.

BACKGROUND

Improvement is desired in the fitting of heat softenable dental guards to the teeth of a user. These dental guards are made out of thermoformable materials, such as thermoplastics. Typically, a user heats water and immerses the guard in the heated water until the plastic becomes pliable. The user then places the guard in this pliable or malleable state in the mouth and applies biting pressure to conform the guard to the teeth and fit the guard to the user. The guard is then cooled to retain the bite pattern in the material.

Plastic trays that underlie the guard have been used in the fitting of the guards in an attempt to reduce undesired deformation of portions of the guard during fitting. However, a problem with these types of devices is that when fitting a single component pliable dental guard, a user's teeth may travel through the pliable material beyond the desired depth reducing or destroying the dental guard ability to separate the teeth and protect from bruxism. Another problem has been the difficulty in properly aligning the dental guard within the user's mouth during the forming process resulting in reduced protection and/or user comfort.

The present disclosure relates to an improved combination of a dental guard structure and a cooperating tray structure that cooperate to improve proper positioning and fitting of the guard and to avoid undesired deformation of portions of the guard, prevent the unintended biting through of the dental guard during the forming process, and improve the fit of the guard and comfort of the fitted dental guard.

SUMMARY

The above and other needs are met by a dental guard and tray.

In one aspect, the dental guard is made of a thermoplastic, is softenable by immersion in heated water, and capable of changing configuration or made malleable when being fitted to a user by heating of the dental guard followed by application of biting pressure by the user to conform or reform portions of the dental guard to the surfaces of the teeth of the user.

The dental guard includes a pair of bite pads positionable upon rear teeth of the user and a connection band that connects between the bite pads and is positionable behind front upper teeth of the user.

The tray is a generally rigid tray made of injection molded plastic to fittingly receive the dental guard during heating and fitting of the dental guard to teeth of the user but remain sufficiently rigid so that during fitting of the dental guard the generally rigid tray does not substantially conform to the tooth surfaces of the user.

The rigid tray includes a pair of bite pad supports and a connecting arc. The bite pad supports each providing a planar depression or well for receiving one of the bite pads. The connecting arc spans between the bite pad supports and has one or more fingers located proximate a midpoint of the arc configured to angle rearwardly and upwardly from the connecting arc so as to underlie and receive the band when the dental guard is received onto the tray.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
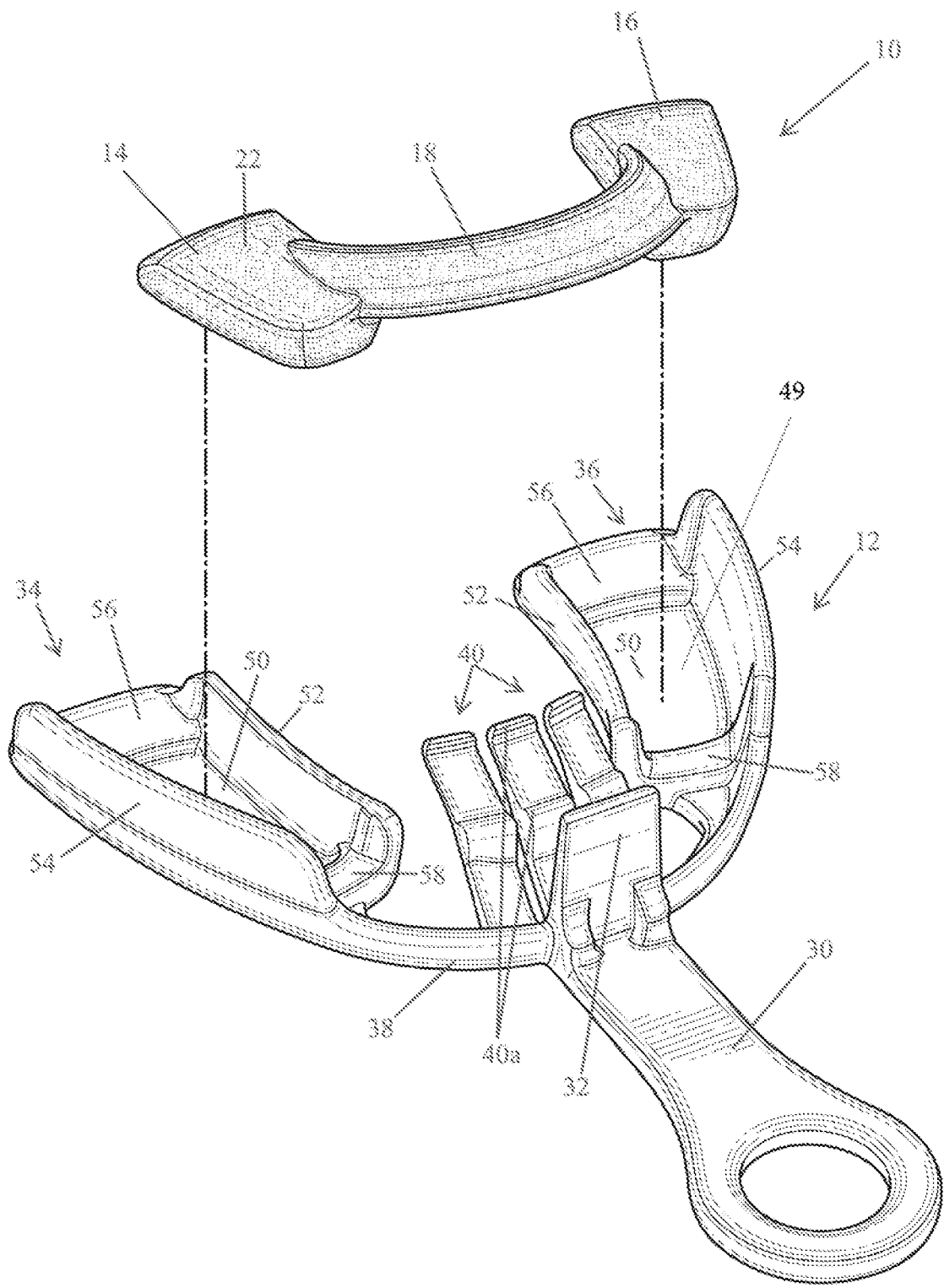
FIG. 1 is an exploded perspective view of a dental guard and tray according to the disclosure.

With reference to the drawings, there is shown a dental guard 10 and a tray 12 according to the disclosure. The guard 10 and the tray 12 advantageously cooperate to avoid undesired deformation of portions of the guard 10 and improve the fit of the guard 10, which improves comfort of the fitted guard 10. While the dental guard 10 and tray 12 are shown in a preferred form upon the upper teeth of a user, it should be understood that the dental guard 10 and tray 12 may be configured for use in connection with a user's bottom teeth. As such, for purposes of the present disclosure, it is noted that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures.

The dental guard 10 is made by injection molding of a single plastic material in a single shot, preferably an ethylene-vinyl acetate copolymer resin, and most preferably an ethylene-vinyl acetate copolymer resin available from DuPont under the name Elvax 450. The guard 10 softens or is made malleable in heated water and hardens when it cools. There is no curing in the nature of chemical bonds formation. A colorant, such as a blue colorant, may be added to the plastic to color the guard 10 to make it easier to see.

The guard 10 may be configured for various uses, such as a mouth guard for teeth clenching during some sports, may be reconfigured for a more robust design for use as a sports guard, or a nightguard for inhibiting bruxism. As shown and described herein, the guard 10 is configured or reconfigured for inhibiting bruxism. In this regard, the guard 10 has bite pads 14 and 16, and a connection band 18 that connects between the bite pads 14 and 16. As shown in the drawings, in a preferred form to the invention, the guard 10 is configured to be applied to the upper teeth and the connection band goes behind the front teeth, but it should be understood that it may also be configured to be applied to the lower teeth.

Figure 3:
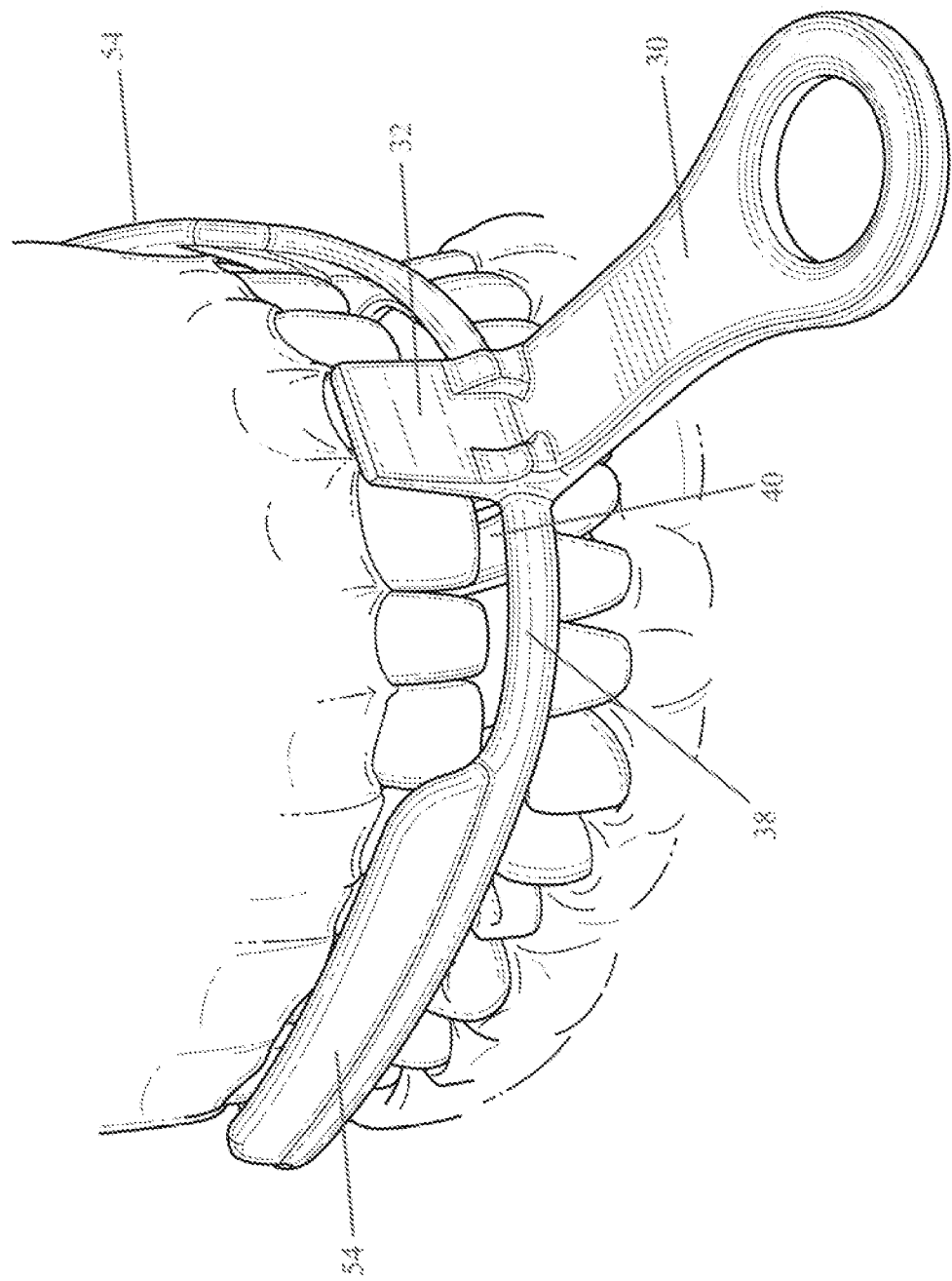
FIG. 3 shows use of the tray in fitting of the dental guard onto teeth of a user.
Figure 4:
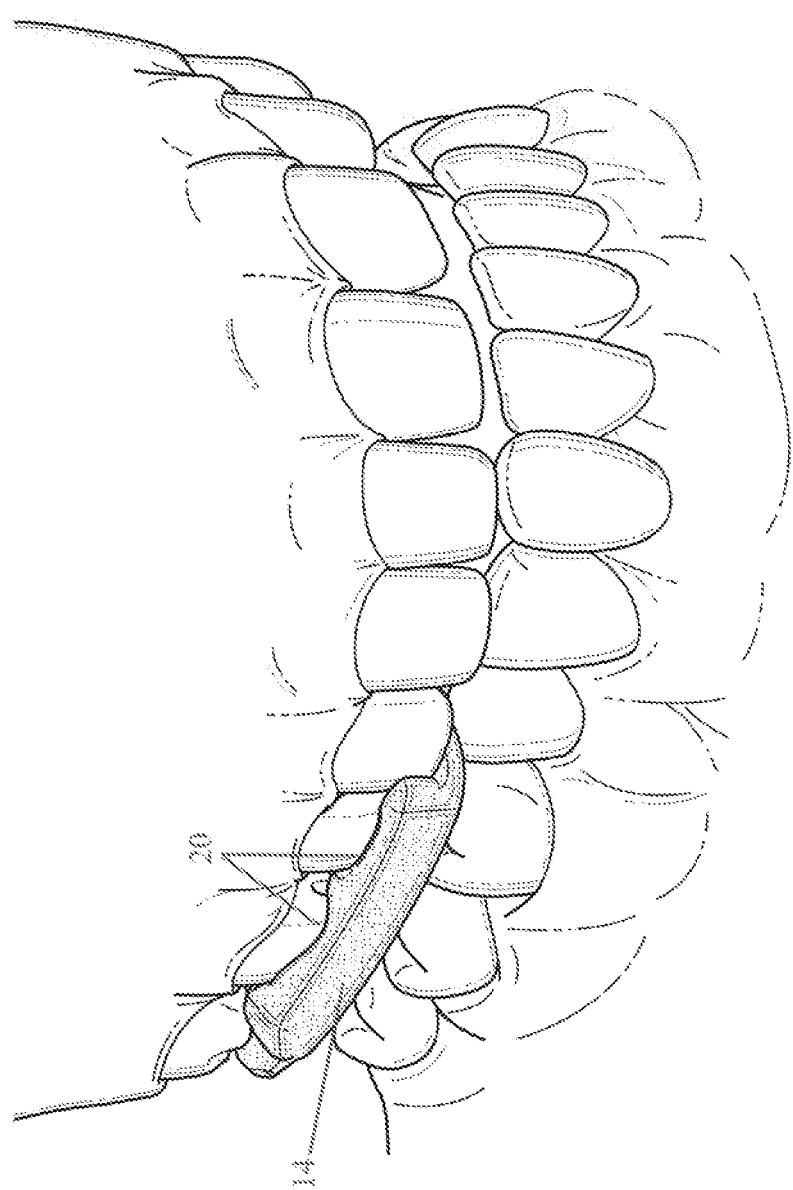
FIGS. 4 and 5 show the dental guard being worn on teeth of a user.
Figure 5:
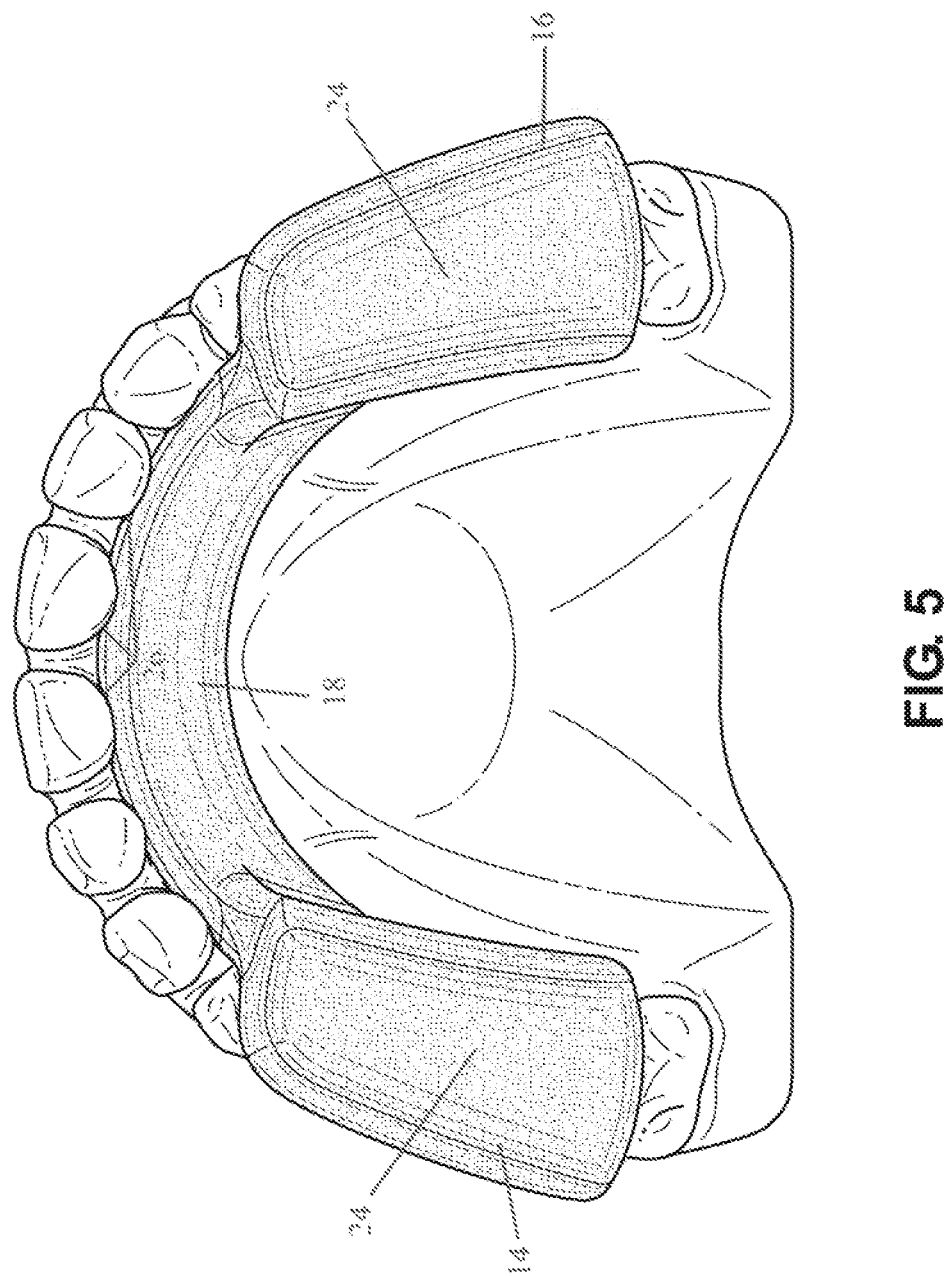
Figure 9:
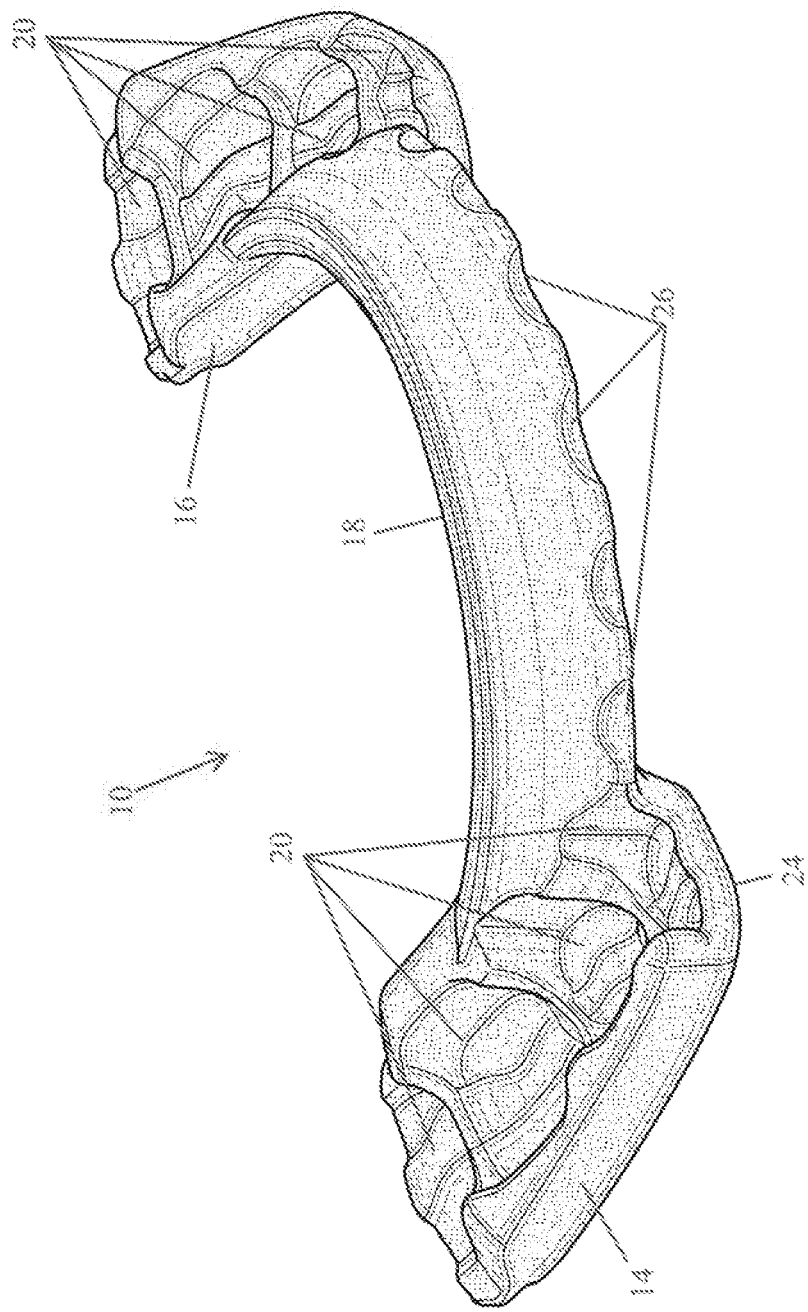
FIG. 9 depicts the dental guard after it has been fit to teeth of a user.

The unformed bite pads 14 and 16 are identical mirror images of one another and are configured to be placed below the rear upper teeth of both sides of the mouth as seen in FIGS. 3, 4, and 5, namely the first bicuspid, second bicuspid, and first molar normally present in a mouth. During fitting of the guard 10, impressions 20 of tooth surfaces of these teeth are formed on upper portions of the bite pads 14 and 16, and on adjacent edges of the band 18, as seen in FIG. 9, and the bite pads 14 and 16 are reconfigured, reconformed, or reformed to the contour of the teeth.

Figure 8:
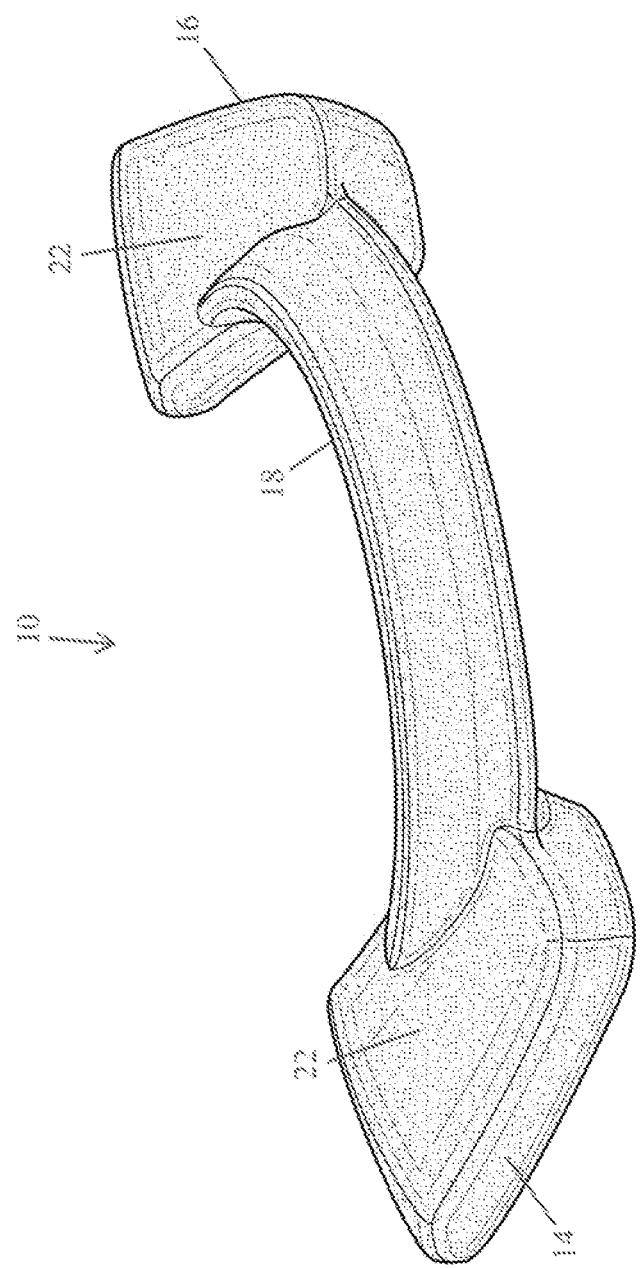
FIG. 8 is a perspective view of the dental guard prior to being fitted to teeth of a user.

As seen in FIG. 8, the bite pads 14 and 16 are each relatively uniformly thick portions of plastic and formed having planar upper surfaces 22 and planar lower surfaces 24. The impressions 20 of the teeth are formed on the upper surfaces 22, while the tray ledges or plateaus 56, 58 serve to limit tooth movement into the tray well 50 and prevent "bite through."

The connection band 18 is an elongate strip of plastic material that is formed in a curve or arc that extends upwardly from an upper interior front corner of each of the bite pads 14 and 16. The band 18 is positioned behind the front teeth as seen in FIGS. 3, 4, and 5. During fitting of the guard 10, impressions 26 of rear tooth surfaces of the front teeth may be formed along a lower frontal edge of the band 18, as seen in FIG. 9, and the band 18 is conformed to the contour of palate and teeth. As seen in FIG. 8, the bite pads 14 and 16 are each relatively uniformly thick portions of plastic and formed having planar upper surfaces 22 and planar lower surfaces 24. The sides of the bite pads 14 and 16 are generally straight and the corners are generally rounded. The bite pads 14 and 16 are generally rectangular in profile but may be narrower at their rear than at their front.

The tray 12 is preferably made of a single plastic material in a single shot and is preferably made of polypropylene with a colorant. The tray 12 is generally rigid and does not soften in heated water but remains sufficiently rigid so that during fitting of the dental guard the tray 12 does not conform to the tooth surfaces of the user. The tray 12 is configured to receive the guard 10, to maintain desired position of the guard 10 relative to the teeth of the user during fitting of the guard 10, and to inhibit or control undesired deformation of the guard 10 during fitting.

The tray 12 with the guard 10 installed on it is placed in heated water, and the tray 12 with the guard 10 is then inserted into the mouth of the user and positioned for fitting of the guard 10 to the teeth of the user. The tray 12 is configured to conform to different arch shapes and assist with desired positioning of the guard in the mouth. Once the guard is desirably positioned, the user applies biting pressure to conform the bite pads 14 and 16 to the teeth of the user. The tray further assists with controlling deformation of the guard.

The tray 12 includes a handle 30, a stop 32, a pair of bite pad supports 34 and 36, and a connecting arc 38 having elongated support members, supports, or fingers 40.

The handle 30 is provided to facilitate immersion of the guard 10 into heated water and positioning of tray 12 relative to the mouth of the user during fitting of the guard 10. The handle 30 extends generally perpendicular to and away from a midpoint of the front of the connecting arc 38.

The stop 32 is located at the juncture of the handle 30 and the connecting arc 38. The stop 32 extends vertically from the juncture of the handle 30 and the connecting arc 38 and has a height and width configured to contact or abut the front upper teeth of the user. The stop 32 serves to inhibit further insertion of the tray 12 into the mouth of the user during fitting of the guard 10 and desirably locate the guard 10 relative to the teeth of the user.

Figure 2:
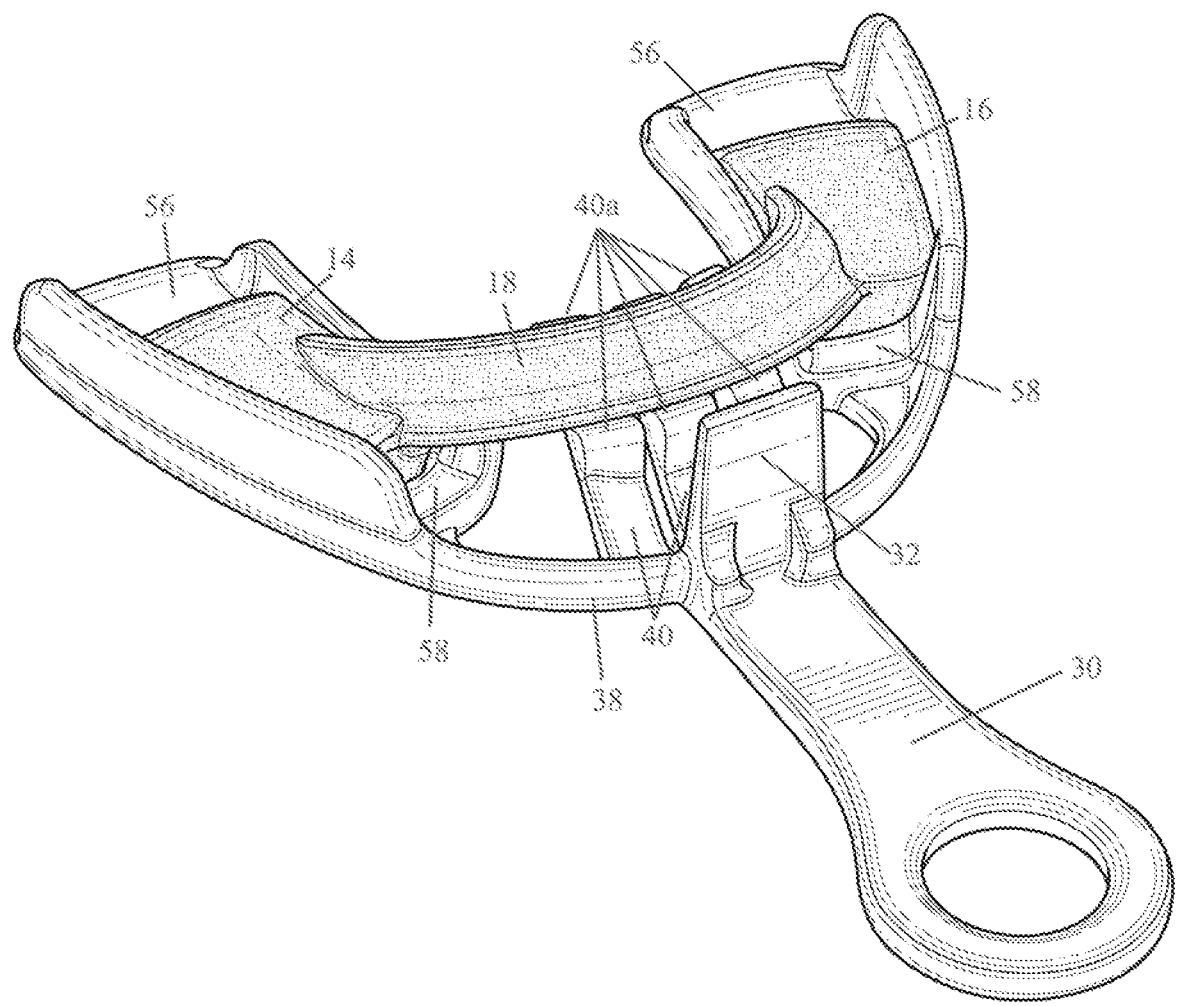
FIG. 2 shows the dental guard installed onto the tray.
Figure 6:
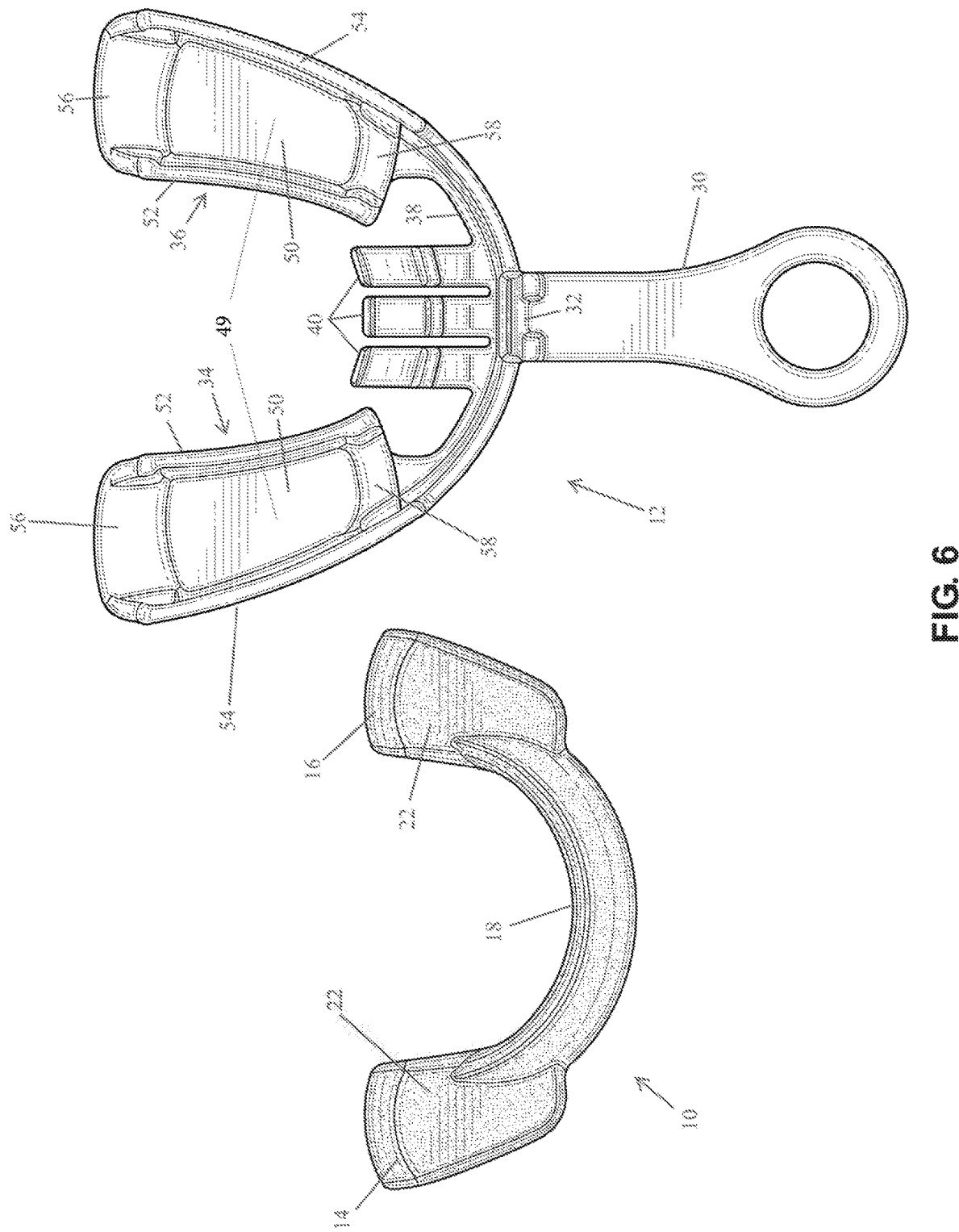
FIG. 6 is an upper plan view of the dental guard and tray.
Figure 7:
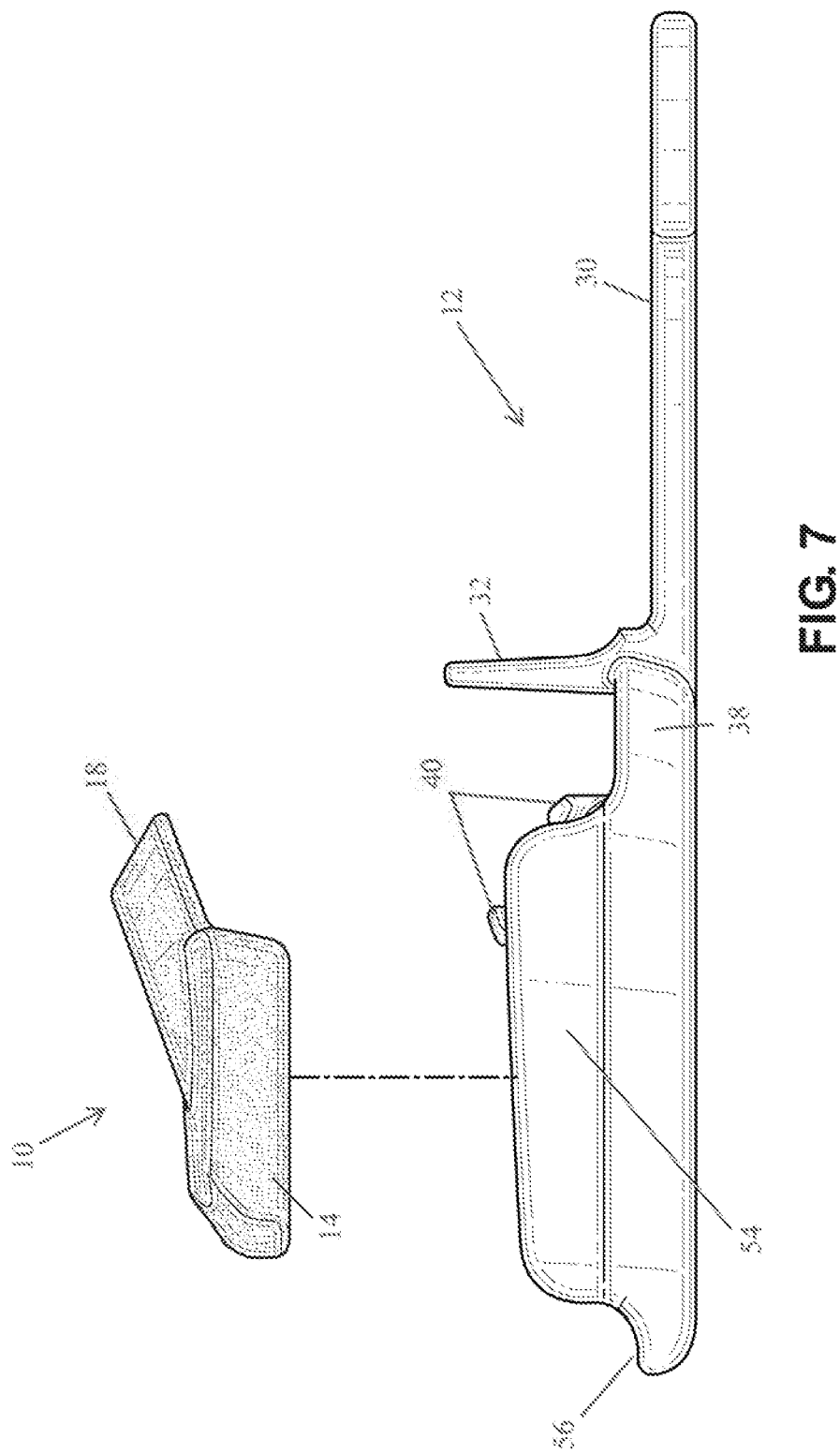
FIG. 7 is a side view of the dental guard and tray.

The bite pad supports 34 and 36 are identical mirror images of one another and are configured to receive the bite pads 14 and 16, respectively, and prevent undesirable deformation of the bite pads 14 and 16 during fitting of the guard 10. As seen in FIGS. 1, 2 and 6, the bite pad supports 34 and 36 each include a recessed well, depression, or recess 49, as best shown in FIGS. 1 and 6, defined by a central planar bottom or floor 50, an inner sidewall 52, an outer sidewall 54, a rear ledge or plateau 56 and a front ledge or plateau 58. The well 49 receives a lower portion of the bite pads 14 and 16, which essentially retains its initial configuration after fitting as this portion is positioned below the level of the rear and front plateaus 56 and 58.

The wells 49 are configured as planar depressions or trays sized and configured to receive the lower portion of the bite pads 14 and 16, while allowing an upper portion of the bite pads to extend beyond the confines of the wells 49. The rear plateaus 56 and front plateaus 58 are configured to abut or contact the tooth's occlusal or grinding surface of the top teeth while the oppositely disposed bottom surface of the bite pad supports are configured to rest upon, contact, or abut the lower teeth of the user. As shown in FIG. 2, the lower portions of the bite pads 14 and 16 are seated within the wells 49 during the fitting of the guard 10 while an upper portion of the bite pads 14 and 16 extend above the wells 49 for deformation by the user's teeth.

The planar surfaces of the well floors 50 desirably provide the reformed or fitted bite pads 14 and 16 still having the planar bottoms 24 as were present in the unfitted guard 10, as seen in FIG. 5. The sidewalls 52 and 54 and the plateaus 56 and 58 provide raised boundaries about the floors 50 to restrain the bite pads 14 and 16 within the wells 49 from deforming during fitting of the guard 10, while not interfering with the jaws or teeth of the user so as to enable the user to apply bite pressure to the pads 14 and 16 during fitting of the guard 10. The sidewalls 52 and 54 also control the direction of the malleable material of the dental guard during the forming process, wherein the material displaced by the user's teeth is allowed to pass between the teeth and the sidewalls 52 and 54 to conform to the outer surfaces of the teeth.

As seen in FIG. 3, the outer sidewalls 54 are of sufficient vertical height to contact against the rear upper teeth of the user to flex the tray to the dental arch width of the user and desirably locate the guard 10 relative to the teeth of the user. The outer sidewalls 54 extend past the bit pads 14 and 16 positioned within the bite pad supports 34 and 36 to contact the tooth buccal surface.

The connecting arc 38 is configured as an arc that spans between the sidewalls 54 and is locatable exterior of the mouth during fitting of the guard 10. The arc 38 cooperates with the stop 32 and the sidewalls 54 to desirably position the fingers 40 within the interior of the mouth of the user during fitting of the guard 10. The fingers 40 are configured to position and support the band 18 of the guard 10 behind and in contact with or abutting the rear of the upper front teeth during fitting of the guard 10.

As seen in FIG. 2, the fingers 40 angle rearwardly and upwardly from the connecting arc 38 so as to underlie and receive the band 18 when the guard 10 is installed onto the tray 12. The fingers 40 each include spaced apart lips 40a that receive and hold both sides of the band 18 to support and maintain the band 18 behind and in contact with the rear of the upper front teeth during fitting of the guard 10. The band 18 would flex and deform away from the teeth and palate during application of biting pressure during fitting of the guard 10 if the fingers 40 with the lips 40a were not maintaining the band 18 in contact with the teeth. The fingers 40 and lips 40a thus hold the band 18 in place so as to avoid the undesired deformation of the band 18 during fitting. The lips 40a also serve to grip the band 18 so as to maintain the guard 10 on the tray 12 during immersion of the guard 10 in heated water prior to fitting. To aid in establishing a proper alignment, the fingers 40 include a central finger and two oppositely disposed side fingers positioned to either side of the central finger so as to abut the teeth and palate offset from the center in order to centrally align the tray and guard.

To accomplish fitting of the guard 10, the guard 10 is installed onto the tray 12 as shown in FIG. 2. The handle 30 is then used to immerse the tray 12 with the guard 10 thereon in heated water for a time sufficient to render the guard 10 in a soft condition for fitting. The tray 12 with the guard 10 thereon is then removed from the heated water and inserted into the mouth of the user so that the stop 32 and the sidewalls 54 abut the teeth of the user as shown in FIG. 2. This serves to orient the guard 10 so that the bite pads 14 and 16 underlie the upper rear teeth and the band 18 is behind and adjacent the upper front teeth. The front teeth are also captured between the fingers 40 and the stop 32. The user then applies a biting pressure to form the impressions 20 and 26 in the guard 10, while the bite pads 14 and 16 and the band 18 are maintained in position to conform to the contour of the teeth. The rear teeth of the user sinks into and thereby deforms or reforms the bite pads 14 and 16. The travel of the teeth through the bite pads is limited by the abutment or contact of the occlusal or grinding surface of the teeth with the rear and front plateaus 56 and 58, which prevents the teeth from extending all the way through the bite pads as a portion of the bite pads reside within the recessed well 49 below the level or surface of the plateaus 56 and 58. The user maintains the pressure while the guard 10 cools to fix the impressions 20 and 26 in the guard 10 to provide a fitted guard, such as shown in FIG. 9. The tray 12 with the fitted guard 10 is then removed from the mouth of the user. The lower portion of the bite pads 14 and 16 which were located within the well 49 form a grinding or bite wall with a thickness of the depth of the well 49. As such, a bite wall is always formed from the lower portion of the bite pads 14 and 16 as the user's teeth are incapable of passing completely through the bite pads 14 and 16 by contact with the plateaus 56 and 58.

From the disclosure, it is shown that a method of reforming a dental guard comprising the steps of providing a thermoplastic dental guard having a pair of bite pads positionable upon the teeth of the user, and providing a tray configured to receive the dental guard, the tray including a pair of bite pad supports wherein each bite pad support has a tooth occlusal contacting surface, a recessed well extending from the tooth occlusal contacting surface configured to receive at least a portion of one of the bite pads therein, and a sidewall extending from the tooth occlusal contacting surface. The thermoplastic dental guard is then warmed to a temperature wherein the thermoplastic dental guard is malleable and it is then positioned upon select teeth of a user. The user then bites down upon the warm thermoplastic dental guard and tray to a position wherein the user's teeth contact the tooth occlusal contact surface to prevent the teeth from contacting the well, thereby allowing a portion of the warm thermoplastic dental guard to pass between the user's teeth and the sidewall of the tray and allowing another portion of the warm thermoplastic dental guard to remain within the well to form a post-procedure grinding or bite wall.

It should be understood that as an alternative to the configuration of the three fingers, the fingers or support member may be configured wider or as an upright T-shaped member wherein the top portion of the T-shaped members spans several teeth.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. A dental guard and tray, comprising:
   a thermoplastic dental guard, the thermoplastic dental guard including
      a pair of bite pads positionable upon the teeth of a user, and
      a connecting band extending between the pair of bite pads; and
   a tray configured to receive the thermoplastic dental guard, the tray including
      a pair of bite pad supports, each bite pad support having a tooth occlusal contacting surface and a well extending from the tooth occlusal contacting surface and configured to receive at least a portion of one of the pair of bite pads therein, each bite pad support including an outer sidewall extending past the at least a portion of the one of the pair of bite pads received within the bite pad support such that an upper edge of the outer sidewall is adapted to contact the tooth buccal surface, and
      a connecting arc extending between the pair of bite pad supports, the connecting arc including
         an elongated support member extending rearwardly and upwardly from a proximal end at a midpoint of the connecting arc to a distal end above the upper edges of the outer sidewalls, wherein the elongated support member includes spaced apart holding lips configured to receive the connecting band of the thermoplastic dental guard between the holding lips and adapted to hold the connecting band of the thermoplastic dental guard behind and in contact with the front teeth for receiving impressions of the front teeth during fitting.

2. The dental guard and tray of claim 1, wherein the tray further includes a stop located on the tray and spaced from the elongated support member such that the tray is adapted to capture a tooth between the elongated support member and the stop.

3. The dental guard and tray of claim 1, wherein each bite pad support also includes an inner sidewall oppositely disposed from the respective outer sidewall.

4. The dental guard and tray of claim 1, wherein each well has a planar floor.

5. The dental guard and tray of claim 1 wherein the elongated support member is a central support member extending from the midpoint of the connecting arc, and the connecting arc further comprising a pair of side support members, wherein each one of the pair of side support members extends from the connecting arc from a position spaced from and on either side of the central support member.

6. A dental guard and tray for use with the teeth of a user, the dental guard and tray comprising:
- a thermoplastic dental guard, the thermoplastic dental guard including
  - a pair of bite pads positionable upon the teeth of the user and
  - a connecting band extending between the pair of bite pads; and
- a tray configured to receive the thermoplastic dental guard, the tray including
  - a pair of bite pad supports each bite pad support receiving at least a portion of one of the pair of bite pads and including an outer sidewall extending past the at least a portion of the one of the pair of bite pads received by the bite pad support such that an upper edge of the outer sidewall is adapted to contact the tooth buccal surface,
  - a connecting arc spanning between the pair of bite pad supports, and
  - an elongated support member extending rearwardly and upwardly from a proximal end at a midpoint of the connecting arc to a distal end above the upper edges of the outer sidewalls,
  wherein the elongated support member includes spaced apart holding lips configured to receive the connecting band of the thermoplastic dental guard between the holding lips and is adapted to hold the connecting band of the thermoplastic dental guard behind and in contact with the front teeth for receiving impressions of the front teeth during fitting.

7. The dental guard and tray of claim 6, wherein the tray further includes a stop extending from the connecting arc and spaced from the elongated support member such that the tray is adapted to capture a tooth between the elongated support member and the stop.

8. The dental guard and tray of claim 6, wherein each bite pad support has a tooth occlusal contacting surface and a well extending from the tooth occlusal contacting surface, the well configured to receive at least a portion of one of the pair of bite pads therein.

9. The dental guard and tray of claim 8, wherein the outer sidewall is adapted to contact the tooth distal from the occlusal surface of the tooth.

10. The dental guard and tray of claim 9, wherein each bite pad support also includes an inner sidewall oppositely disposed from the respective outer sidewall.

11. The dental guard and tray of claim 8, wherein each well has a planar floor.

12. The dental guard and tray of claim 6 wherein the elongated support member is a central support member extending from the midpoint of the connecting arc, and the connecting arc further comprising a pair of side support members, wherein each one of the pair of side support members extends from the connecting arc from a position spaced from and on either side of the central support member.

13. A dental guard and tray, comprising:
- a thermoplastic dental guard, the thermoplastic dental guard including
  - a pair of bite pads positionable upon the teeth of a user,
  - a connecting band extending between the pair of bite pads; and
- a tray configured to receive the thermoplastic dental guard, the tray including
  - a pair of bite pad supports, each bite pad support of the pair of bite pad supports having a recess configured to receive at least a portion of one of the pair of bite pads therein, each recess being defined by
    - a floor,
    - a front plateau elevated above the floor,
    - a rear plateau elevated above the floor,
    - an outer sidewall extending from the floor between the front plateau and the rear plateau and past the at least a portion of the bite pad received within the bite pad support such that an upper edge of the outer sidewall is adapted to contact the tooth buccal surface,
  - a connecting arc extending between the pair of bite pad supports, the connecting arc including an elongated support member extending rearwardly and upwardly from a proximal end at a midpoint of the connecting arc to a distal end above the upper edges of the outer sidewalls, the elongated support member including a pair of spaced apart holding lips configured to receive the connecting band of the thermoplastic dental guard between the holding lips and adapted to hold the connecting band of the thermoplastic dental guard behind and in contact with the front teeth for receiving impressions of the front teeth during fitting.

14. The dental guard and tray of claim 13 wherein each bite pad support of the pair of bite pad supports further comprises an inner wall oppositely disposed from the outer wall, wherein the outer wall has a height above the floor greater than the height of the inner wall.

15. The dental guard and tray of claim 13, wherein the tray further includes a stop located on the tray and spaced from the elongated support member such that the tray is adapted to capture a tooth between the elongated support member and the stop.

16. The dental guard and tray of claim 13 wherein the elongated support member is a central support member extending from the midpoint of the connecting arc, and the connecting arc further comprising a pair of side support members extending from the connecting arc wherein one side support member is positioned on either side of the central support member.

* * * * *